(12) United States Patent
Tomas Fernandez et al.

(10) Patent No.: US 11,922,645 B2
(45) Date of Patent: Mar. 5, 2024

(54) IMAGING SYSTEM

(71) Applicant: Medtronic Navigation, Inc., Louisville, CO (US)

(72) Inventors: Xavier Tomas Fernandez, Jamaica Plain, MA (US); Andre Souza, Boylston, MA (US); Robert A. Simpson, Shirley, MA (US); Kyo C. Jin, Durham, NH (US); Hong Li, Boxborough, MA (US); Xiaodong Tao, Westwood, MA (US); Patrick A. Helm, Milton, MA (US); Michael P. Marrama, Ayer, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 17/206,032

(22) Filed: Mar. 18, 2021

(65) Prior Publication Data

US 2022/0301200 A1    Sep. 22, 2022

(51) Int. Cl.
*G06T 7/33* (2017.01)
*G06T 11/00* (2006.01)

(52) U.S. Cl.
CPC ............... *G06T 7/33* (2017.01); *G06T 11/00* (2013.01); *G06T 2207/20221* (2013.01)

(58) Field of Classification Search
CPC .. G06T 7/33; G06T 2207/20221; G06T 11/00
See application file for complete search history.

(56) References Cited

U.S. PATENT DOCUMENTS

| | | |
|---|---|---|
| 5,592,939 A | 1/1997 | Martinelli |
| 5,772,594 A | 6/1998 | Barrick |
| 5,913,820 A | 6/1999 | Bladen et al. |
| 5,983,126 A | 11/1999 | Wittkampf |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,697,972 B2 | 4/2010 | Verard et al. |
| 7,751,865 B2 | 7/2010 | Jascob et al. |
| RE44,305 E | 6/2013 | Foley et al. |
| 8,644,907 B2 | 2/2014 | Hartmann et al. |

(Continued)

FOREIGN PATENT DOCUMENTS

| | | |
|---|---|---|
| DE | 102008023330 A1 | 11/2009 |
| EP | 3545896 A1 | 10/2019 |
| WO | 2019233422 A1 | 12/2019 |

OTHER PUBLICATIONS

International Search Report and Written Opinion regarding International Application No. PCT/US2022/018859, dated Jul. 13, 2022.

(Continued)

*Primary Examiner* — Matthew Salvucci
(74) *Attorney, Agent, or Firm* — Harness, Dickey & Pierce, P.L.C.

(57) ABSTRACT

Disclosed is a system and method for operating an imaging system. The imaging system may move or be moved to acquire image data of a subject at different positions relative to the subject. The image data may, thereafter, be combined to form a single image.

19 Claims, 8 Drawing Sheets

(56) References Cited

U.S. PATENT DOCUMENTS

| | | |
|---|---|---|
| 8,842,893 B2 | 9/2014 | Teichman et al. |
| 9,737,235 B2 | 8/2017 | Hartmann |
| 10,489,912 B1 * | 11/2019 | Brailovskiy ......... H04N 13/204 |
| 2002/0018589 A1 | 2/2002 | Beuker et al. |
| 2004/0199072 A1 | 10/2004 | Sprouse et al. |
| 2009/0207971 A1 | 8/2009 | Uhde et al. |
| 2015/0297177 A1 * | 10/2015 | Boctor .................. A61B 34/30 |
| | | 901/47 |
| 2020/0268334 A1 | 8/2020 | Gemmel et al. |
| 2020/0405399 A1 | 12/2020 | Steinberg et al. |

OTHER PUBLICATIONS

International Search Report and Written Opinion regarding Application No. PCT/US2022/019861, dated Jul. 7, 2022.

* cited by examiner

IMAGING SYSTEM

CROSS-REFERENCE TO RELATED APPLICATIONS

This application includes subject matter similar to U.S. application Ser. No. 17/205,940 filed Mar. 18, 2021. The entire disclosures of each of the above applications are incorporated herein by reference.

FIELD

The present disclosure relates to an imaging system, and particularly to a moveable imaging system and acquisition of image data therewith.

BACKGROUND

Imaging systems may acquire image data of a subject. The image data may be used to generate images. The images may be displayed for viewing by a user and/or further analyzed and/or augmented for various purposes. The images may illustrate a selected portions of a subject.

An imaging system that acquires image data of the subject may acquire a plurality of image data projections of the subject. The plurality of projections may be acquired at a plurality of positions of the imaging system relative to the subject. For example, a system may include an arm or a projector that moves in space relative to a subject to acquire a plurality of positions of image projections relative to the subject.

Further areas of applicability will become apparent from the description provided herein. The description and specific examples in this summary are intended for purposes of illustration only and are not intended to limit the scope of the present disclosure.

SUMMARY

This section provides a general summary of the disclosure, and is not a comprehensive disclosure of its full scope or all of its features.

An imaging system may include a portion that moves relative to a selected position. A subject may be placed at the position for acquiring image projections thereof. The imaging system may acquire one or a plurality of image projections, including image data, at a plurality positions relative to the subject.

The plurality of image projections may be acquired to generate images of views of the subject at a plurality of positions, including a plurality of locations and/or a plurality of orientations. For example, the imaging portion of the imaging system may translate axially (i.e., along a Z-axis) relative to the subject to acquire an image projections at a plurality of positions along the axis. As the imaging portion moves, the imaging portion may move relative to the subject or a selected pose relative to the subject. For example, the imager may change a positioned in at least one degree of freedom other than movement along the Z-axis. For example, the imaging system may tilt, rotate, sag, etc. Accordingly, a system, such as a system including a processor module, may evaluate the image data and/or additional data signals to determine an alignment for generating a composite or combination image based upon the plurality of image projections of the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
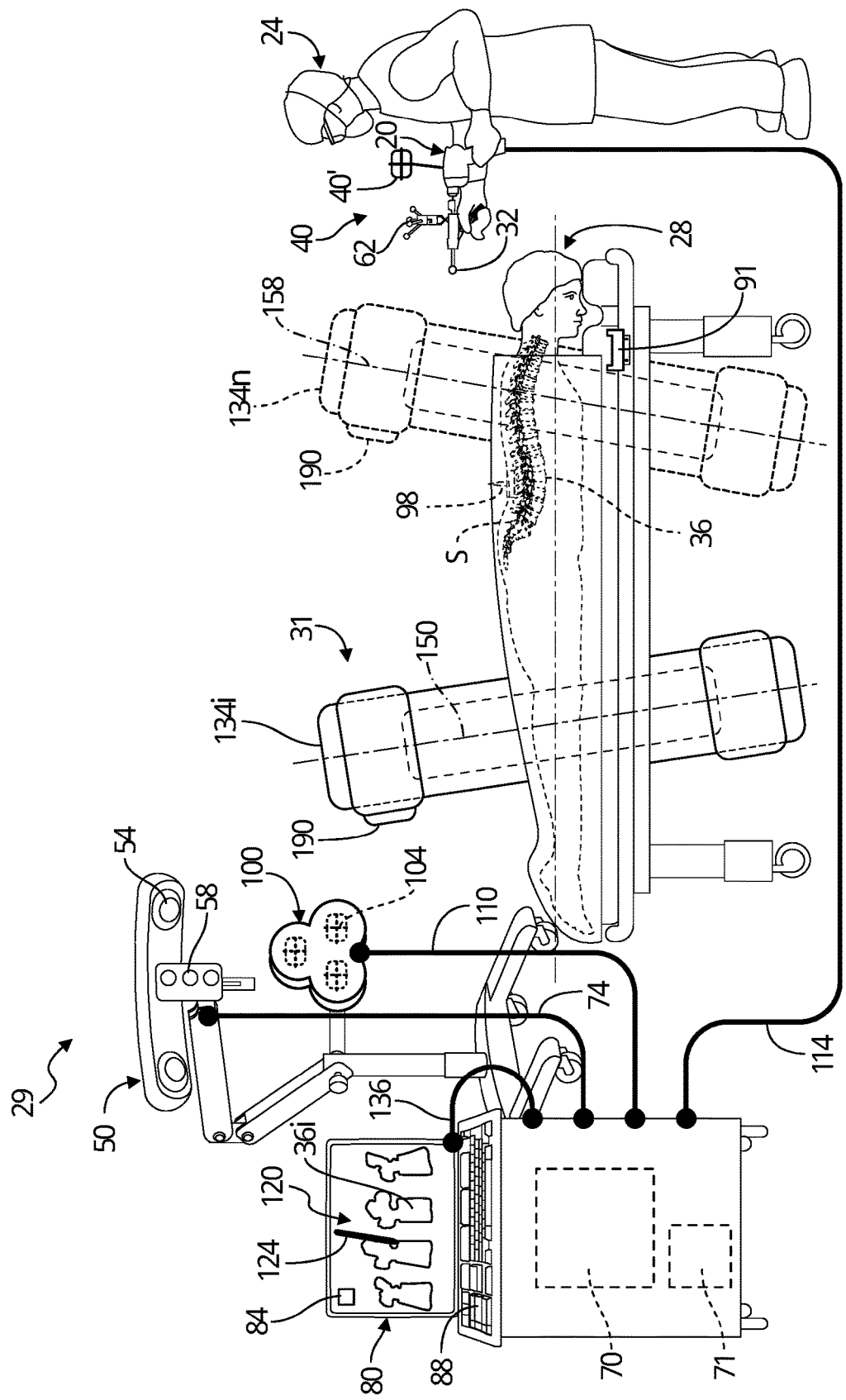
FIG. 1 is an environmental view of a procedure room with an imaging system and navigation system, according to various embodiments.

FIG. 1 is an environmental view of a procedure system that may be used during a procedure during which an instrument, such as a powered drill assembly 20, may be used by a user 24, to perform a procedure on a subject (e.g. a patient) 28. In various embodiments, the powered drill assembly 20 may include a powered dissection tool 32 for performing a select procedure, such as forming a burr hole in a cranium of the subject 28, operating on one or more a vertebra 36, or other selected procedure. The instrument 20, according to various embodiments, may include an appropriate motor component such as the LEGEND MR8ø and/or LEGEND EHS STYLUSø motor systems, sold by Medtronic, Inc. The motor component may include a motor that is powered such as a pneumatic powered, such as the LEGEND MR7ø motors although other power motors or drives may be used such as electric power motors LEGEND EHS STYLUSø motors. It is understood, however, that the powered drill assembly 20 may be used for performing other procedures such as a removal of material relative to and/or in the vertebrae.

For example, the powered drill assembly 20 may be operated to remove a portion of the vertebra in a selected procedure, including a laminectomy procedure or other appropriate spinal procedure. Further, it is understood that the powered drill assembly 20 may be used to perform a procedure on a non-living subject such as to drill a hole in an airframe, an automotive frame, or the like. Accordingly, the powered drill assembly 20 is not required to be used with a living subject, such as a human patient.

The powered drill assembly 20 may include a motorized drill that is tracked and/or navigated relative to the subject 28 according to various embodiments with various systems and/or for various procedures. A navigation system 29 may include a tracking system, as discussed further herein, and may include a tracking device 40 that may be connected to the powered drill assembly 20 to track a position or pose of a tool relative to the subject 28, such as the vertebra 36. Generally, the pose includes both a coordinate location (such as a location in 3D space) and an orientation (such as at least one or more, including three, degrees of freedom). Thus, a pose or position may include a selected amount of degrees of freedom, such as six degrees of freedom information regarding an object (e.g., the instrument 20). Appropriate tracking systems include those disclosed in U.S. Pat. No. 8,842,893, incorporated herein by reference. It is understood that image data may be acquired of the subject 28 to create images, as discussed herein. To acquire the image data, an imaging system 31 may be used prior to beginning a procedure or after a procedure has begun, the procedure may include operation of the powered drill 20. The imaging system 31 may include an O-arm® imaging system sold by Medtronic, Inc. and/or may include those disclosed in U.S. Pat. Nos. 7,188,998; 7,108,421; 7,106,825; 7,001,045; and 6,940,941; all of which are incorporated herein by reference. The imaging system 31, therefore, may include an annular gantry include an annular volume in which a detector and/or source are rotated around the subject 28. Other possible imaging systems include C-arm fluoroscopic imaging systems which can also generate three-dimensional views of the patient 28, such as the ZIEH M VISION® RFD 3D imaging system sold by Ziehm Imaging GmbH having a place of business at Nuremberg, Germany.

The tracking system may be a part of the navigation system 29 to assist in performing selected procedures, such as a surgical procedure on the subject 28, and may include those as generally known in the art. For example, navigation systems may include those as disclosed in U.S. Pat. Nos. 5,772,594; 5,913,820; 5,592,939; 5,983,126; 7,751,865; and 8,842,893; and 9,737,235 and those disclosed in U.S. Pat. App. Pub. No. 2004/0199072, all incorporated herein by reference. Tracked positions may be displayed on images or relative to images due to registration of a position of a subject or real space to an image space, also as disclosed in the U.S. patents and publications as incorporated above. Further, tracking systems may include the Stealth Station S8® tracking system, and AxiEMú tracking system, all sold by Medtronic Navigation, Inc.

The tracking systems may include various features such as an optical tracking systems, EM tracking systems, ultrasonic tracking systems, or the like. Nevertheless, as illustrated in FIG. 1, for example, a tracking system may include one or more localizers that may include portions that include cameras and/or antennas for receiving/and or transmitting a signal for tracking. Localizers may include an optical localizer 50 that includes one or more cameras 54 that may detect or view: the tracking device 40 connected to the power drill 20. The localizer 50 including the cameras 54 may emit a selected radiation, such as infrared radiation from emitters 58, that is reflected by one or more trackable portions 62 that are associated with the tracking device 40. The trackable portions 62 may be viewed by the cameras 54 and a signal may be transmitted to a navigation processor unit 70. The navigation processor unit 70 may include various features, such as a navigation probe interface (NPI), as discussed further herein. The navigation processor unit 70 may also include a coil array controller (CAC) for various types of tracking systems. Various features such as the NPI, the CAC, or other portions may be provided as separate units from the navigation processor unit 70 or separate modules for interacting with various portions of the navigation system, as is generally known in the art.

The localizer 50 may communicate with the navigation processor unit 70 via a selected communication line 74. The communication line 74 may be a wired or a wireless communication with the navigation processor unit 70. The navigation processor unit 70 may communicate with a selected system, such as a workstation, a terminal, or the like that includes a display system or display module 80 having a display screen 84 and one or more user inputs 88. It is understood, however, that the display screen 84 may be separated for the processor unit 70 and/or in addition thereto, such as a projected display, a headset display (e.g., augmented reality systems). The user inputs 88 may include a keyboard, a mouse, a touch screen, or other tactical input. Further inputs may also include a foot switch, verbal inputs, visual inputs, or the like.

A subject tracking device 98 may also be connected, such as fixed, relative to the subject 28. In various embodiments, the subject tracking device 96 may be fixed to one or more of the vertebra 36 and/or other portion of the subject 28. Generally, the subject tracking device is fixed relative to a selected portion of the subject 28. In various embodiments, for example, the subject may be fixed to a subject support 90 (such as with a mount 91) to which the subject 28 is fixed, at least for a selected period. Thus, the subject tracked 98 is generally fixed relative to the subject 28 at least for a selected period, such as while acquiring image data, during a procedure, etc.

In various embodiments, alternative or additional tracking systems may be provided, such as an electromagnetic tracking systems including an electromagnetic tracking array, such as a coil array 100. The coil array 100 may include one or more coil elements 104 that emit and/or receive an electromagnetic signal from an electromagnetic (EM) tracking devices, such as the subject tracking device 98 associated and/or connected to the patient 28 or a tracking device 40' connected to the power drill 20. The coil array 100 may communicate with navigation processing unit 70 via a communication line 110 similar to and/or the same as the communication line 74 from the localizer device 50 to the navigation processing unit 70. Further, each of the tracking devices may communicate with the navigation processing unit 70 via selected communication lines such as communication line 114 so that a position of the selected tracking devices, including tracking device 40 and tracking device 98 may be determined with a navigation processing unit 70. It is understood that one or more than one tracking system may be used simultaneously and/or serially during the selected procedure.

The display screen 84 may display an image 120 of a portion of the subject 28, such as a vertebra image 36i of the vertebra 36. The image 120 may be based on or generated with image data acquired with the imaging system 31 as discussed above. Displayed relative to the image 120 and/or superimposed on the image 120 of the patient 28 may be a graphical representation, also referred to as an icon, 124. The icon 124 may represent a position such as a pose, of the powered drill assembly 20 that may include the tool 32, relative to the subject 28. The represented position may also be of only a portion of the assembly 20. The position of the powered drill assembly 20, or a portion thereof, relative to the subject 28 may be determined by registering the powered drill assembly 20 relative to the subject 28 and thereafter tracking the location of the powered drill assembly 20 relative to the subject 28.

Registration may include various techniques, such as those disclosed in U.S. Pat. Nos. RE44,305; 7,697,972; 8,644,907; 8,238,631; and 8,842,893; and U.S. Pat. App. Pub. No. 2004/0199072, all incorporated herein by reference. Generally, registration includes a mapping between the subject space and the image space. This may be done by identifying points in the subject space (i.e. fiducial portions) and identifying the same points in the image (i.e. image fiducials). A map of the image space to the subject space may then be made, such as by the navigation system. For example, points may be identified manually, automatically, or a combination thereof in the image data, such as in the image 120.

Related points may be identified in a subject space, such as defined by the subject 28. For example, the user 24 may identify a spinous process in the image 120 and an instrument tracked by one or more of the tracking systems, including the localizers 50, 100, may be used to identify a spinous process at the vertebrae 36. Once an appropriate number of points are identified in both the image space of the image 120 and the subject space of the subject 28, a map may be made between the two spaces. The map allows for a registration between the subject space defined by the subject, also referred to as a navigation space, and the image space defined by the image 120. Therefore, the instrument, or any appropriate portion, may be tracked with a selected tracking system and a poise of the instrument may be identified or represented relative to the image 120 with the graphical representation 124.

As discussed above, registration of the powered drill assembly 20 relative to the subject 28, such as with or to the subject tracking device 98, may be made at a selected point in a procedure. The image 120 may then be displayed on the display screen 84 and a tracked location of the powered drill assembly 20 may be displayed as the icon 124 relative to the image 120. The icon 124 may be superimposed on the image 120 to display a pose of at least a selected portion of the powered drill assembly 20, such as a distal end, of the tool 32 powered by the powered drill assembly 20. As briefly noted above, the pose or position may include a location that includes three degrees of freedom in space (for example, including at least one of a XYZ position) and a selected number (e.g., three) degrees of freedom orientation information location (for example, including at least one of yaw, pitch and roll orientation). The pose may be determined and/or calculated by the navigation processing unit 70 and communicated to the display device 80 via a selected communication line, such as a communication line 130. The communication line 130 may be a wired or wireless or other appropriate communication line.

Further, it is understood that the navigation processor unit 70 may include various features such as a selected processor (e.g., an application specific integrated circuit (ASIC), general purpose processor or the like). The navigation processor unit 70 may also include a memory system (e.g., non-transitory memory systems including spinning hard disks, non-volatile solid state memory, etc.) that includes selected instructions, such as those to perform the tracking, registration, superimposing of the icon 124 on the image 120, or the like. Therefore, the determined pose of the powered drill assembly 20 (for example the selected portion of the powered drill assembly 20, as discussed further herein), may be displayed relative to the subject 28 by the icon 124 relative to the image 120. The user 24 may then be able to view the display screen 84 to view and/or comprehend the specific pose of the selected portion of the powered drill assembly 20 relative to the subject 28 by viewing the display 84.

Figure 2A:
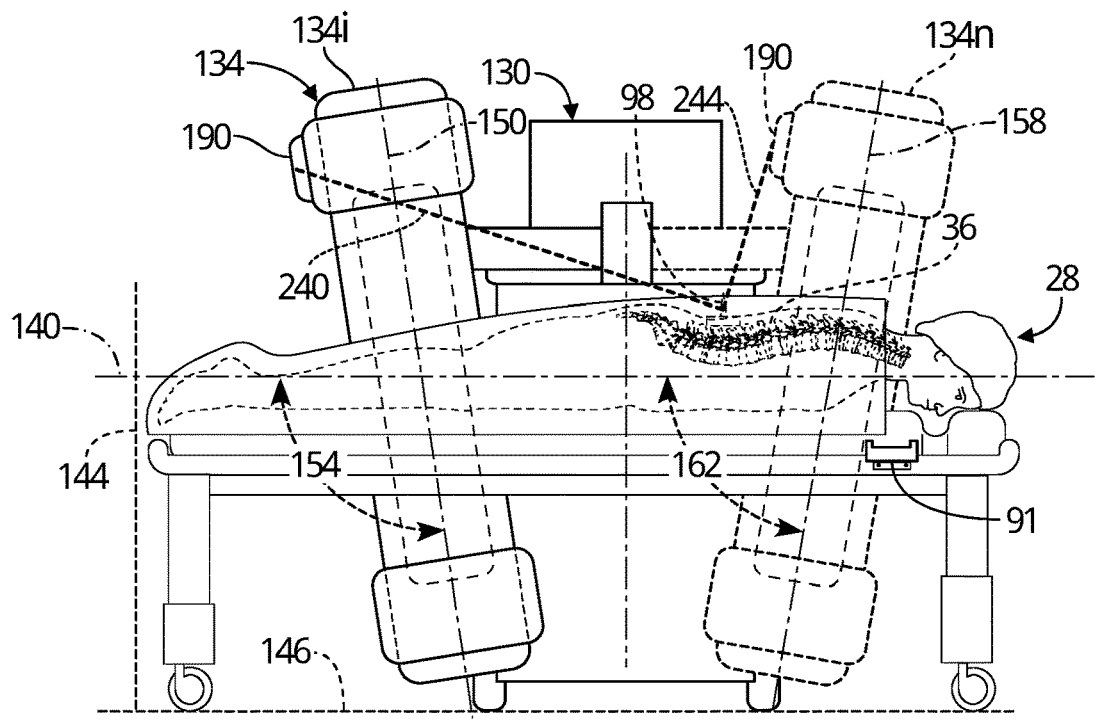
FIG. 2A is a side elevation view of an imaging system at a first and second position, according to various embodiments.
Figure 2B:
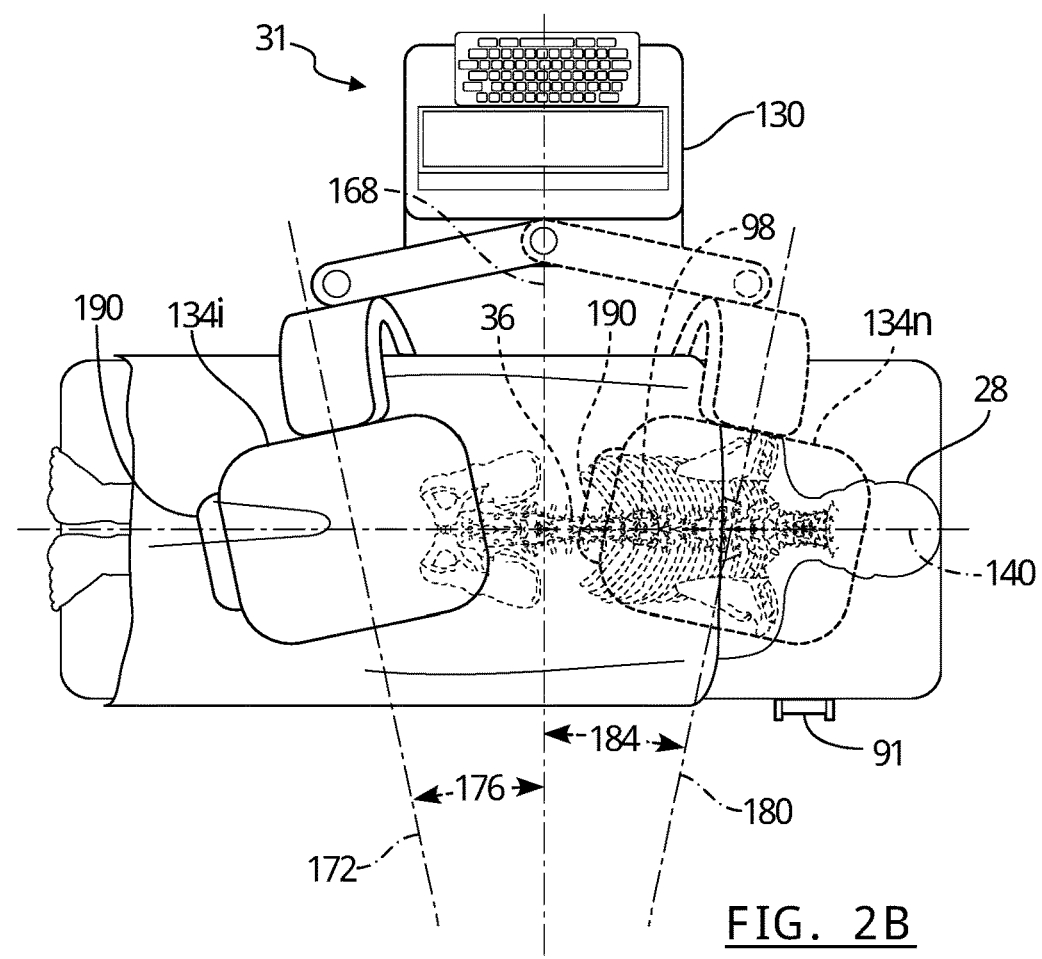
FIG. 2B is a top plan view of the imaging system of FIG. 2A.

With continued reference to FIG. 1 and additional reference to FIG. 2A and FIG. 2B, the imaging system 31, also referred to as an imager, may include a plurality of portions, such as a first or base portion 130 and a gantry or movable portion 134. The gantry portion 134 may be movable relative to the subject 28 and/or the base 130. The gantry 134 may move, for example, such as between a first position 134i and a second or final position 134n. It is understood, as illustrated in FIGS. 1, 2A, and 2B that the gantry 134 may move between the initial position 134i and a final position 134n. Although two positions are illustrated, a plurality of positions greater than two positions may be used. For example the gantry 134 may move through a total of three positions, four positions, or any appropriate number of positions to acquire image data of the subject 28. Thus, one or more intermediate positions may be determined for movement of the gantry 134, although they are not illustrated. The intermediate position(s) may be between the first position 134i and the final position 134n, and/or outside of the first position 134i and the final position 134n. The gantry 134 may, for example, include a maximum range of movement relative to the console or base portion 130 and an appropriate number of movements or positions of the gantry 134 may be selected or achieved to ensure image data acquired at all possible positions or enough image data is acquired to achieve a selected final image for display with the display device 84. For example, the positions of the imaging system 31, including the gantry 134 (e.g., the first, final, and any possible selected intermediate positions), for collection of image data may be selected and/or determined based on a selected dimension of a combined image, as discussed herein.

As illustrated in FIGS. 1, 2A, and 2B, the gantry 134 may be at different positions relative to the subject 28 at the different gantry positions 134i, 134n. For example, the subject 28 may extend along an axis 140. It is understood that the axis 140 may be of the subject 28 or any appropriate axis that may be define a reference axis or plane for movement of the gantry 134. The axis 140 may also be reference to as a Z-axis that may be used to define or determine at least one degree of freedom of movement of the imaging system 31. Relative to the axis 140 may be a perpendicular axis 144. The perpendicular axis 144 may be perpendicular to the long axis 140 and/or perpendicular to a floor or surface 146, such as a floor on which the console 130 is positioned and/or fixed. Further, the subject 28 and the axis 140 may be fixed relative to the surface 146.

As illustrated in FIG. 2A, the gantry 134 at the initial position 134i may extend along or define an axis 150 that is at a first angle 154 to the axis 140. At the final position 134n, the gantry 134 may extend along or define an axis 158 that is at a second angle 162 relative to the axis 140. As illustrated in FIG. 2A, the first angle 154 at the position 134i and the angle 162 at the second position 134n may differ. Accordingly, as discussed further herein, image projections acquired at the first position 134i may differ, such as not being aligned along the Z-axis, from those acquired at the second position 134n.

Additionally, with reference to FIG. 2B, the gantry 134 may also be at other orientations at the first position 134i and the final position 134n. The console 130 and the gantry 134 may be viewed from a top view, as illustrated in FIG. 2B, and viewed relative to an axis 168 that extends perpendicular to the axis 140 through the subject, but parallel to the base or floor 146. The gantry 134 in the first position 134*i* may extend along an axis 172 that forms a first angle 176 relative to the axis 168 and the gantry 134 at the second position 134*n* may extend along or oriented along an axis 180 that extends at a second angle 184 relative to the axis 168. As illustrated in FIG. 2B, the angle 176 may differ from the angle 184 and/or position the gantry 134 at a different orientation relative to the subject 28, such as the axis 168.

As illustrated in FIGS. 2A and 2B, therefore, it is understood that the gantry 134 may be at a different positions relative to the subject 28 to acquire a plurality of image projections of the subject 28. The different projections according to the different orientations may, therefore, differ and not be initially aligned relative to each other, as discussed further herein.

It is also understood, however, that various other movements of the gantry 134 may occur during an acquisition of projections at a plurality of positions. For example, the gantry may move, such as _wobble: due to a weight distribution of the gantry 134 relative to the based 130. Further, the gantry 134 may move in other ways due to movement of the gantry 134 to acquire the plurality of projections along a length or along the axis 140 of the subject 28. Accordingly, the movement of the gantry 134 as illustrated in FIGS. 2A and 2B is merely exemplary of a process discussed further herein.

With continued reference to FIGS. 1, 2A, and 2B, the subject or patient tracker (DRF) 98 may be tracked relative to the subject 28 for a selected period with the navigation system 29 including the relevant or appropriate tracking system. The tracking system including the respective localizers 50, 100 may be used to track the DRF 98 during a selected procedure and/or for a period of time. Further, the tracking systems may track other appropriate tracking devices, such as the tracking device 40 associated with the instrument 20. In addition, a tracking device, also referred herein to as an imaging tracking device 190, may be associated with the gantry 134. The tracking device 190 may be tracked with the respective tracking system included with the navigation system 24. Therefore, the position of the gantry 134 may be determined with the navigation system 24, similar to determining a position of the various other instruments or portions with respective tracking devices. In various embodiments, for example, the tracking device 190 may be tracked relative to the subject tracking device 98 during the selected procedure, such as acquiring image data of the subject 28. This allows the position of the gantry 134 to be determined relative to the subject 28, where the position of the subject 28 may be determined based upon the position of the patient tracker 98.

The position of the gantry 134, therefore, may be determined at a plurality of positions relative to the subject 28. As discussed above, the gantry 134 may move between at least the positions 134*i* and 134*n* and/or other selected or determined intermediate positions. The position of the gantry 134 may be tracked at both the gantry positions 134*i* and 134*n*. Thus, the position, which includes location and orientation of the gantry 134, may be determined at a plurality of positions relative to the subject 28. As discussed above, image data may be acquired of the subject with the imaging system 31 at the plurality of positions of the gantry 134. The positions of the gantry may change, such as by the various angle and/or translational position relative to the subject 28.

Figure 3:
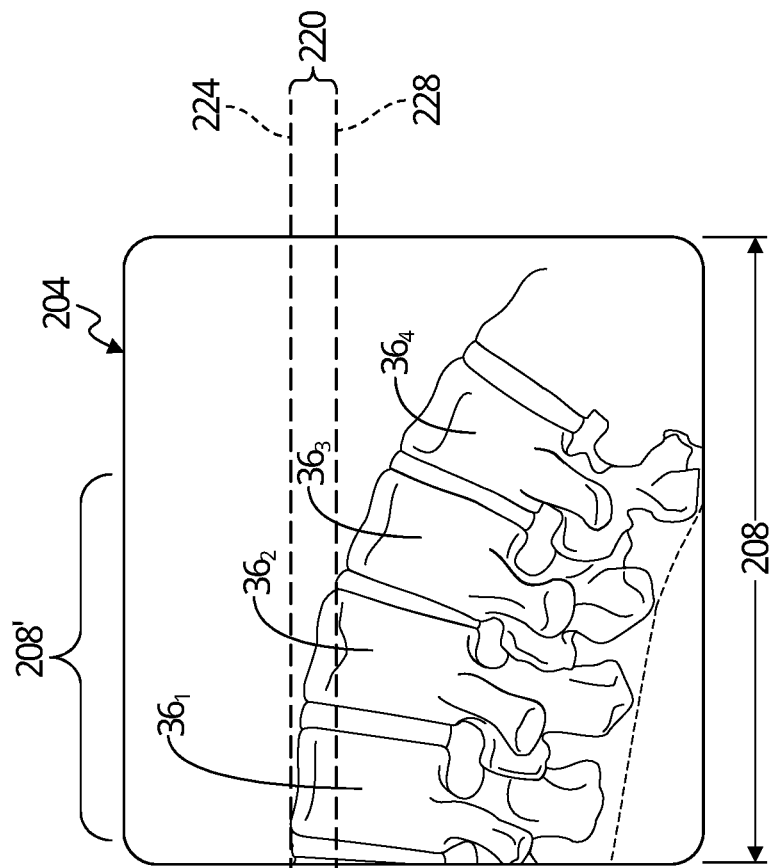
FIG. 3 is a schematic illustration of a first and second projection of the imaging system at a first and second position, according to various embodiments.
Figure 3:
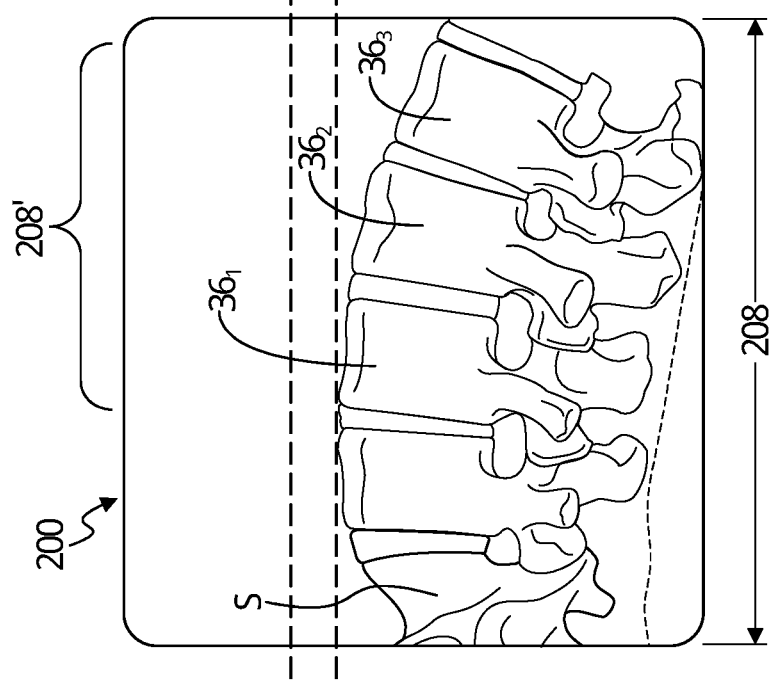

With continued reference to FIGS. 1-2B and additional reference to FIG. 3, the imaging system 31 may acquire a plurality of projections through the subject 28. In various embodiments, the imaging system 31 may include a x-ray imaging system that may acquire a plurality of projections of the subject 28. The imaging device 31 may acquire a plurality of projections that may be two-dimensional projections and/or three-dimensional image or image data. For example, image data at each position may include a three-dimensional image projection or reconstruction based on a plurality of two-dimensional image data.

Further, the plurality of projections may be combined in a selected manner, as discussed further herein, to generate a selected image such as a three-dimensional image, a long film image, or the like. In various embodiments, a long film image may be an image that is longer than what is acquired with a single acquisition projection through the subject 28 with the imaging system 31. Accordingly, a plurality of projections or images may be combined to form a combination image in a selected manner, such as _stitched: together to form a long film.

With reference to FIG. 3, for example, the imaging system 31 may acquire a first image projection 200 and a second image projection 204. Both of the image projections may have a selected dimension 208. The dimension 208 may be about 8 centimeters (cm) to about 20 cm, including about 12 cm to about 16 cm, and further including about 15 cm. The selected projections 200, 204 may have the dimension 208 that is determined or a maximum dimension based upon the imaging system 31. For example, a detector of the imaging system 31 may have a maximum dimension that is the dimension 208 or allows a maximum projection dimension of 208. Any single one image projection of the subject 28 may be limited by the physical dimensions of the imaging system 31.

As illustrated in FIG. 3, the two projections 200, 204 may include selected portions of the subject, such as vertebrae 36. For example, the first projection 200 may be acquired at the position 134*i*. The projection 200 may include selected vertebrae such as a first vertebrae $36_1$, $36_2$, and $36_3$. The three vertebrae $36_1$, $36_2$, and $36_3$ may be viewed in the projection 200 that is acquired with image data that may be acquired with the gantry 134 in a selected first position, for example the position 134*i*. The second projection 204 may include a selected number of vertebrae, such as the vertebrae $36_2$ and $36_3$. The second projection 204 may further include the vertebrae $36_4$. Accordingly, the second projection 204 may include additional image data that is then included in the first image 200. Further, the second image 204 may not include image data that is in the first projection 200, such as a portion of a sacrum S of the subject 28. As discussed further herein, the two images 200, 204 may be stitched together in a selected manner, as discussed further herein, to obtain an image that includes a dimension greater than the dimension 208.

The two images 200, 204 are acquired with the gantry 134 that may be initially selected to have only be linearly displaced from each other, such as along the axis 140 (Z-axis). Movement of the gantry 134, however, may create the projections through the subject 28 at slightly different positions that are not only due to a direct translation or straight translation along the axis 140. As discussed above, the gantry 134 may include a plurality of positions relative to the subject 28, such as due to a movement at an angle relative to the axis 140 and/or the surface 146. As discussed above, the gantry 134 may be moved to selected positions including the first position 134*i* and the second position 134*n* that are not a straight linear translation along the axis 140. Therefore, while the two projections 200, 204 may initially include image portions that are along the axis 140 they may differ from one another, such as due to or by a distance 220 exemplary illustrated between a first line or plane 224 and a second line or plane 228. It is understood that the distance 220 is merely exemplary, and that the difference between the two projections 200, 204 may be due to any movement of the gantry 134 including a vertical translation away from or toward the surface 146, a rotation or angle change relative to the axis 140 and/or the surface 146, or other appropriate difference. Therefore, the gantry 134 may not only move in a linear translational along the axis 140 to acquire the multiple projections 200, 204, but may include other movement relative to the axis 140. The relative movements may generate projections that include the spatial difference 220 between the two projections 200, 204.

It is understood that the number of projections may be any appropriate number of rejections such as one or at least one projection acquired at each position of the gantry 134. Therefore, the illustration of two projections 200, 204 is merely exemplary for the current discussion. Further the type of movement may be a complex movement that includes both a rotational movement and a translational movement other than along the axis 140. For example, the gantry 134 may both rotate relative to the axis 140 and include a vertical movement relative to the surface 146 and the axis 140. Accordingly a complex or plurality of movements may occur during the acquisition of a plurality of image projections of the subject 28 with the imaging system 31.

In various embodiments, however, the navigation system 29 may track or determine a position of the gantry 134 at each or during each image acquisition or image data acquisition. During the acquisition of the first projection 200, the gantry tracking device 190 may be tracked and the position determinative of the navigation system 29. Similarly during the acquisition of the second projection 204, the gantry tracking device 190 may be tracked to determine a second position of the gantry 134 during the acquisition of the second projection 240. The position of the imaging portion of the gantry 134 may be known relative to the position of the gantry 134, therefore the position of the gantry that is tracked may be used to determine the position at various acquisitions.

As noted above, the image projection 200 or image data 200 may be acquired with the imaging system 31. The projection 200 may be acquired with a gantry at the initial position 134*i*. As discussed above the imaging system 31 may include the imaging system tracker 190. The imaging system tracker may be tracked with a navigation system 29 to allow for a determination of a pose or position of the gantry 134 relative to the patient tracking device 98 during acquisition of the projection 200. The position during the acquisition of the projection 200 may be noted and saved with the navigation system 29 and/or appropriate system, such as with a memory associated with a processor system 70, such as a memory 71. Therefore, the image projection 200 may have a determined and stored pose of the gantry 134 during the acquisition thereof. Similarly, the tracking system may track a position of the gantry 134 during the acquisition of the second projection 204, such as in the position 134*n*. The position of the gantry 134 during the acquisition of the second projection 204 may also be stored with the imaging system or the navigation system 24, as discussed above.

As is understood by one skilled in the art, the imaging system tracking device 190 may be tracked as may be the patient tracking device 98. Accordingly, a position or pose of the gantry 134 may be determined relative to the patient tracker when in the first position, such as schematically illustrated by the line 240 and a position when the gantry is in the second position 134*n* may be determined such as schematically illustrated by the line 244. Thus, the position of the gantry 134 during the acquisition of the plurality of projections through the subject 28 may be known or determined during the acquisition of the projections. Each of the projections, such that the projections 200, 204 may include the position information regarding the gantry 134, as noted above. It is understood, as discussed above, that the number of acquisitions and/or positions of the gantry may be any appropriate number and two is illustrated merely for the current discussion. Further, it is understood that any appropriate amount of position data and projections may be acquired at any one of the positions of the gantry relative to the subject 28.

With reference to FIG. 2A and FIG. 2B, at each position of the gantry for acquisition of image data 134*i*, 134*n* the position of the patient tracker 98 may be determined and the tracked position of the imaging system tracker 190 may be determined. Accordingly, the schematic line 240 may be understood to be a transformation or a correlation of a tracked position of the patient and a tracked position of the imaging system at the first position 134*i*. Similarly the schematic line 244 may be understood to be a tracked position of the patient relative to or transformed to a tracked position of the imaging system at the second position 134*n*. Accordingly, a determination of a position of the imaging system relative to a reference, such as the axis 140, and the subject 28, may also be determined at each of the gantry positions. This also allows for each of the projections 200, 204 to be registered to the subject 28, as noted above, at least because the position of the imaging system and the subject 28 are determined and known for each projection 200, 204.

The position of the gantry 134 at the first position 134*i* may include or be determined relative to the axis 150 and may be an orientation of the gantry 134 relative to the axis 140 at the angle 154. The axis 150 of the gantry 134 may be tracked to determine with the navigation system 29 while acquiring the projection 200. Similarly, the axis 158 may be determined relative to the axis 140 by tracking the gantry 134 by acquiring the second projection 204. The angle 162 may include or illustrate a portion of the position information relative to the axis 140 and may identify a difference of position between the first position of the gantry 134*i* and the second position of the gantry 134*n*. It is understood, however, that the gantry tracking device 190 may allow for tracking of the gantry 134 and all position information.

At each of the positions, therefore, a transformation of the tracked position of the patient with the patient tracker 98 to the tracked position of the gantry 190 may be made. As illustrated in FIGS. 2A and 2B, therefore, two transformation or correlations of the position of the patient and the position of the gantry 134 may be determined. Further, at each of the positions of the gantry 134*i*, 134*n* a transformation or correlation of a position of the gantry 134 relative to a reference, such as the axis 140 may be determined therefore a first transformation or position may be determined at the first gantry position 134*i* and a second transformation or position may be determined at the second gantry position 134*n*.

According to various embodiments, therefore, a transformation of the position of the gantry during the acquisition of the projections may be made. The projection 200 may be transformed to the position of the image 204, or vice versa.

Such a process allows for combining various images and correcting for or removing distortion or error due to a non-linearity of the acquisition of the images. The transformation allow for aligning the two projections, 200, 204 as discussed further herein.

For example, a transformation of the first position of the gantry to the second position of the gantry may be determined such as using auto-registration systems or techniques such as those included with the StealthStation® S8 navigation system, sold by Medtronic, Inc. having a place of business in Minnesota. For example, with reference to Equation 1:

$$T_{ISiISn} = T_{ISRi} * (T_{ISPi})^{-1} * (T_{ISPn}) * (T_{ISRn})^{-1} \quad \text{Eq. 1}$$

Where $T_{ISiISn}$ represents a transformation of the position of the gantry at the first position 134*i* (ISi) and the position of the gantry of the second position 134*n* (ISn). This may be determined by combining the various correlations or transformations of the patient to the imaging system. This may include a product of TERI that is a determination or transformation of the tracked first position of the gantry and the determined position of the gantry, an inverse of $T_{ISPi}$ that is a transformation of a tracked position of the patient and a tracked position of the imaging system at a first position, a transformation $T_{ISPn}$ of a tracked position of the patient at the second position to a tracked position of the imaging system at the second position, and an inverse of $T_{ISRn}$ which is a position of the imaging system at the second position transformed to a tracked position of the imaging system.

Figure 4:
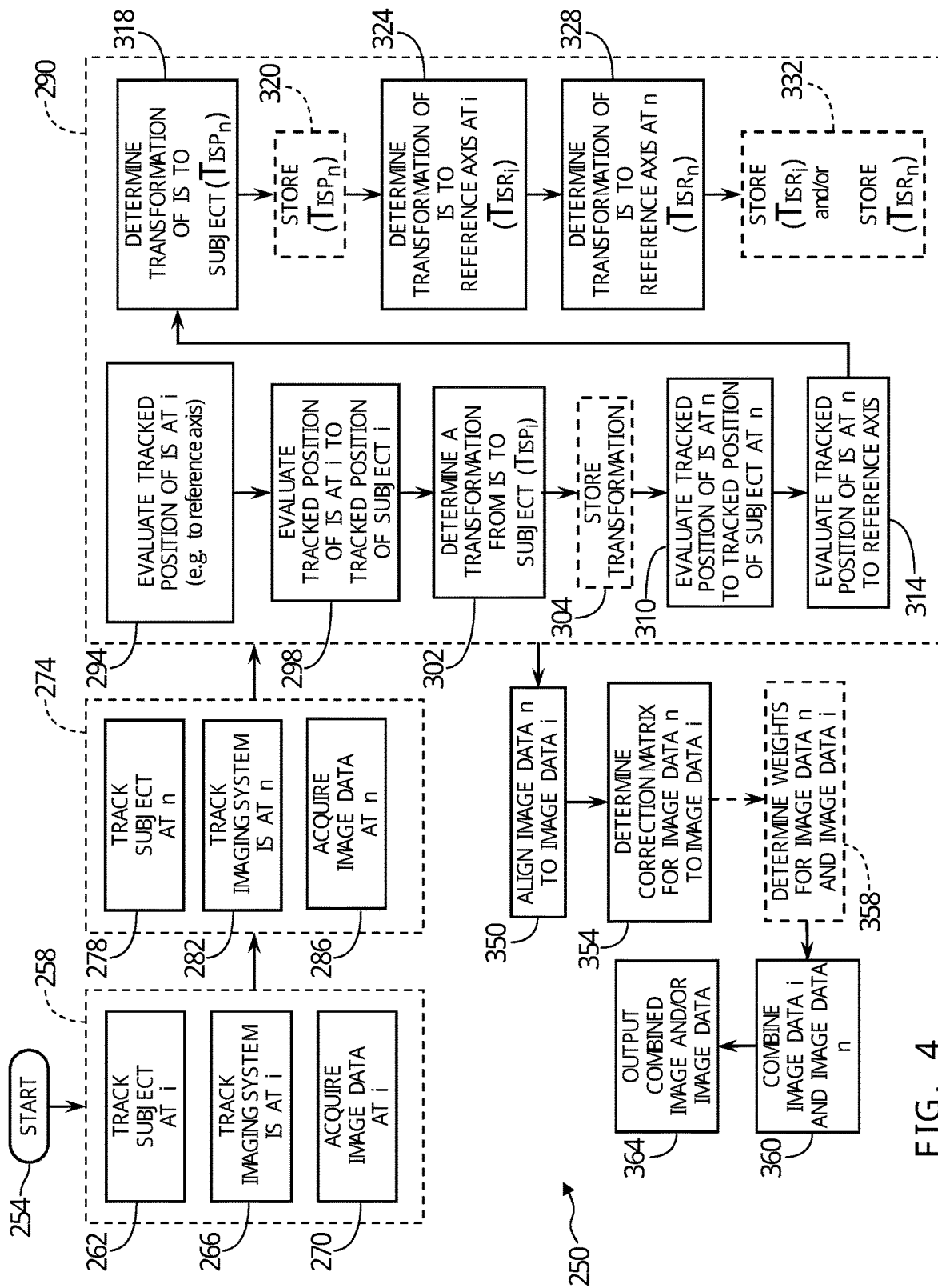
FIG. 4 is a flow chart of a procedure for aligning a first and second image, according to various embodiments.

With continued reference to FIGS. 1-3 and additional reference to FIG. 4, a method 250 of acquiring image data, such as the first projection 200 and the second projection 204 and determining and/or correcting for movement or positions of the gantry 134 that is in addition to a predetermined selected movement, such as a linear or straight translation relative to a reference, such as the translation along the axis 140 (Z-axis). It is understood that the gantry 134 includes various imaging systems, as described above, and therefore reference to movement or the positioning of the gantry may be understood to include and/or refer to movement or positions of the imaging portions that acquire the image data of the subject 28.

The method 250 may be initiated by the user 24 in a start block 254. The start block 254 may include various procedures, such as preparing the subject 28, attaching the patient tracker 98 relative to the subject 28, initiating the navigation system 29, or other appropriate procedures or steps. Nevertheless in the start block 254 the method 250 may be initiated to acquire in a line image data.

The method 250 includes various processes or steps that may be further subdivided such as a first subroutine or process of an initial registration and image acquisition subprocess or subroutine 258. The subprocess 258 may include various portions that may occur in any appropriate manner and/or order is understood by one skilled in the art. The subject 28 may be tracked at the initial gantry position 134*i* in block 262. The tracking of the subject at the initial position in block 262 may include tracking the subject tracker 98 when the gantry 134 is in the initial position 134*i*. Additionally, the imaging system may be tracked at the initial position in block 266. Tracking the imaging system (IS) at the initial position may also be performed with the navigation system 29 that includes the various tracking systems and may be used to track the IS tracking device 190. Accordingly, the subject 28 may be tracked at the initial position in block 262 and the imaging system 31 may be tracked in the initial position of block 266. The imaging system 31 may acquire image data at the initial position in block 270. The initial image data projection may include the projection 200 as discussed above. Accordingly, the image data may be acquired at a tracked position of the subject 28 and a tracked position of the imaging system 31, including the gantry 134. Thus, the image data is acquired at the initial position 134*i* may have associated therewith the tracked position of the subject block 262 and the tracked position of the imaging system in block 266.

As discussed above, the imaging system 31 may be used to acquire a plurality of projections of the subject. As illustrated in FIG. 4 the process 250 exemplary illustrate the acquisition of initial image data in block 258 and a second subprocess to acquire subsequent image data referred to as _n:. It is understood that any appropriate number of projections may be acquired and that a second image acquisition subprocess 274 may refer to a second or any appropriate number of image projections. Accordingly, the process 250 may be used to acquire a selected number of projections to generate a final image volume of a selected dimension, such as length, of the subject 28. In various embodiments, as discussed above, the vertebrae 36 may be imaged and the length of the image may be selected to include a selected number of the vertebrae 36 of the spinal column of the subject 28. It is further understood that an image acquisition may be used to acquire additional image data, such as portions of a pelvis, sacrum S, leg bones, or the like. Nevertheless the subprocess 274 may include the acquisition of any appropriate number of projections in addition to the initial projection.

The subprocess 274 may include tracking the subject at a position n in block 278. The position n may be any appropriate position other than the initial position, such as a position after the initial position and may include the second position, a third position, or any appropriate position. As used herein, therefore, _n: may refer to any appropriate position. The imaging system may be tracked at the position n at block 282. The imaging system 31 may acquire image data of the subject in block 286. The position of the imaging system in block 282 may be the position of the gantry 134*n* as discussed above. As exemplary illustrated in FIGS. 2A and 2B, the imaging system may have an initial position 134*i* and a second position or _n: position 134*n*. The subprocess 274 may include the acquisition of the image data at the 134*n* position such as the second projection 204, while tracking the subject 278 in block 278 and the gantry in block 282. Accordingly, the imaging system 31 may be used to acquire a plurality of projections such as an initial projection and other, including subsequent, projections with a tracked position of the gantry 134 and the subject 28 during the acquisition of the image data.

As discussed herein, due to the tracking of the imaging system, including the gantry 134 and the subject 28 while acquiring the image data, the acquired image data projections are registered to the subject. Thus, the image data 200, 204 may be used to define a coordinate system that is registered (i.e., transformed) to a subject space defines by the subject 28.

The tracked information regarding the subject 28 and the gantry 134 may be used to determine movement of the imaging system, generate a stitched or combined model or image of the subject 28 based on or including a plurality image data acquisition at a plurality of positions of the imaging system including the gantry 134. The tracked information and the acquired image data may then be further analyzed at any appropriate time, such as after each of the individual image data acquisitions. It is further understood, the process 250 need not occur in the specific order of acquiring the image data and the subprocesses 258, 274 prior to any registration and/or transformation, such as generated in a transformation subprocess 290.

The subprocess 290 may be referred to as a transformation or correction process by evaluating the tracking information of the subject and the imaging system of the various subprocesses 258, 274 discussed above. For example, an evaluation of the tracked position of the imaging system at position i may be made, such as its position relative to a selected reference, which may include the axis 140 in block 294. Further, an evaluation of the tracked position of the imaging system may be made relative to the subject at position i in block 298. The evaluation of the tracked position of the imaging system at the initial position i relative to the subject 28, such as with the patient tracker 98, may be used to determine a transformation of the imaging system to the subject $T_{ISPi}$ in block 302. The transformation $T_{ISPi}$ may be made to transform a position of the imaging system, such as the gantry 134 to the subject 28. The transformation $T_{ISPi}$ may optionally be stored for further recall or later recall in block 304. The initial imaging system to patient transformation may be used as a reference for later transformations. In other words, later image data may be aligned to the initial image data for further processing, such as combining the plurality of image data. It is understood, however, that any appropriate transformation may be used as a reference as discussed further herein.

Further in the transformation subprocess 290, an evaluation regarding the tracked position of the subject and the imaging system at the position n may also be made in block 310. An evaluation of a tracked position of the imaging system relative to a reference, such as an imaging plane including the axis 140 may also be made in block 314. A transformation $T_{ISPn}$ may be determined of the imaging system (IS) to the subject at the second or other position _n: when the second image data is collect in block 318. The transformation may be similar to that discussed above regarding the initial position, but regarding the later or second positions, as noted above, identified as _n:. After determining the transformation of the imaging system to the subject at the position n, the transformation may be stored, optionally, in block 320. As discussed above, storing various data may include storing in the memory system 71, and/or any appropriate memory system. The selected processing system, such as the processor system 70, may then recall the data from the selected memory for further analysis, such as by executing selected instruction that may be included in various applications, programs, or the like.

With the evaluated and/or stored data regarding the tracked positons of the imaging device and the subject for each of the image data acquisitions, transformations regarding the position of the gantry 134 to the tracked position may be made based upon an evaluation of the position of the imaging system at positions i and n to a selected reference, such as from blocks 294, 314. Thus, a determination of a transformation of the imaging system to the reference axis or portion at the initial position $T_{ISRi}$ may be made in block 324 and a determined transformation of the imaging system to reference axis or plane at the second or other positions $T_{ISRn}$ may be made at block 328. Again, the transformations may be optionally stored in a selected memory system in block 332. In this manner, the transformations of the imaging system, such as the gantry 134, to the subject may be determined and/or recalled to allow for a correction of a unselected misalignment of the plurality of image data at the various positions relative to each other. Thus, transformations of the imaging system to a reference axis at the various positions, such as i and n, ($T_{ISRi}$ and $T_{ISRn}$) may be used for further analysis of the image data.

Figure 5:
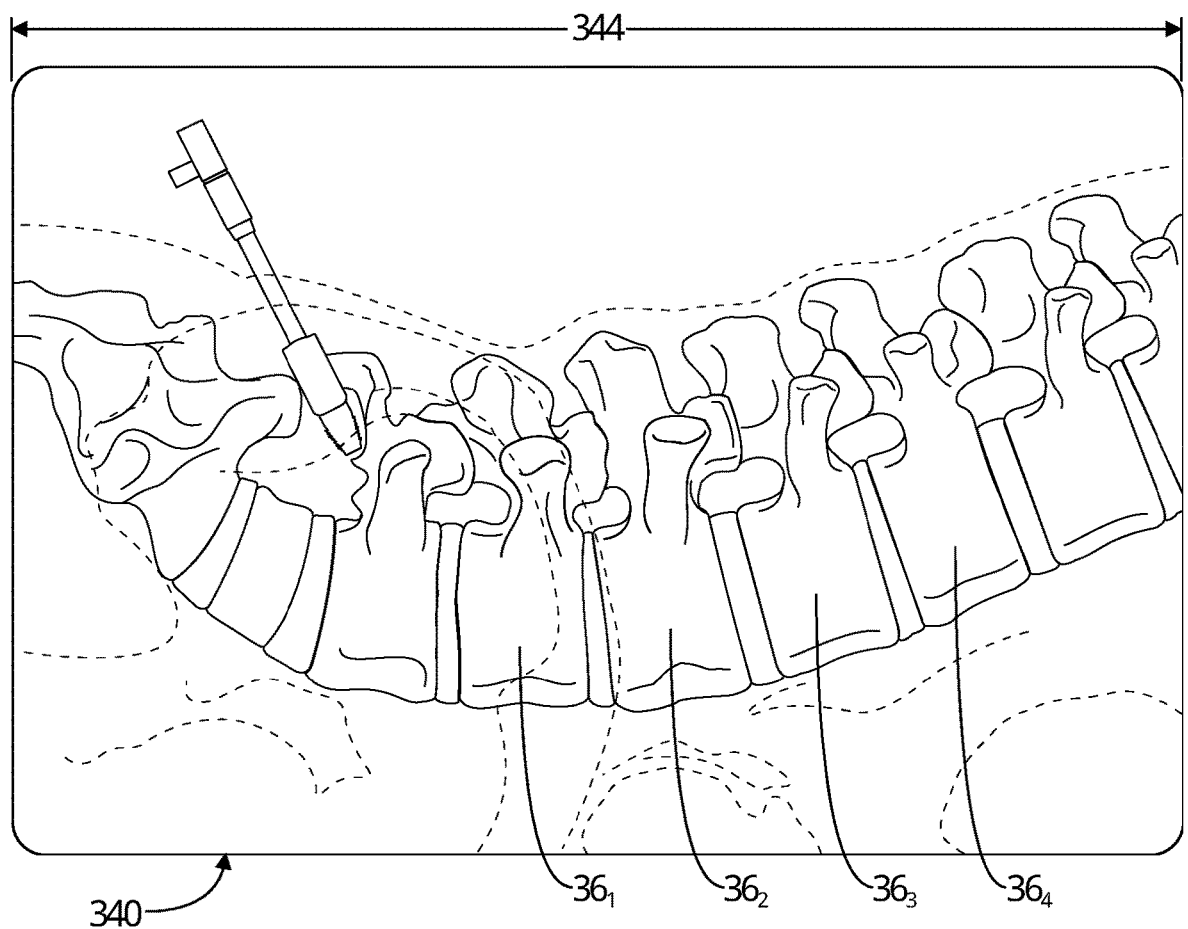
FIG. 5 is a schematic illustration of a combined image, according to various embodiments.

Based upon the various transformations discussed above, the image data acquired at the various positions may be aligned to allow for a stitching or combination of the various images to a combined or final image or image data that is a long image relative to the individual projections. As discussed above and illustrated in FIG. 3, each of the projections 200, 204 may include a selected length 208 of the subject. The length 208 may be substantially identical to the two images based upon the position of the image or gantry 134 and various geometries thereof. Further, each of the image projections may include a selected overlap 208' that may overlap between subsequent or selected images. The combination of the images may include a total length that is greater than an initial length, such as a combined or stitched image 340, as illustrated in FIG. 5, and which may also be illustrated as the image 84. The image 340 may include a dimension 344 that is generally along the same axis as the dimension 208 of the projections 200, 204. The dimension 344 may be greater than the dimension 208 and may include all selected portions of the subject 28 as selected by the user 24. For example, the composite of stitched image 340 may include four of the vertebrae $36_1$, $36_2$, $36_3$, and $36_4$ and other portions of the anatomy, such as the sacrum S. Thus, the stitched image 340 may include a greater amount of image data than may be acquired with any one of the projections of the imaging system 31.

The imaging system, as noted above, may acquire a plurality of projections, such as the projections 200, 204. These may be stitched together to form the stitched image or model 340. It is understood, that the stitched image 340 and the individual selected projections may be two-dimensional, three-dimensional, or otherwise reconstructed into a three-dimension from a plurality of two-dimensional projections. In various embodiments, for example, the imaging system 31 may acquire a plurality of projections at each of the positions, such as the initial position 134i and the second position 134n and generate a three-dimensional model regarding the subject at each position. The individual projections may be two-dimensions and/or the three-dimensional models that may then be stitched to form the final or selected to stitch image or model 340, as illustrated in FIG. 5. Thus, it is understood that the stitched image 340 may be two-dimensional, three-dimensional, or any of the appropriate dimensions. The various transformations determined in the process 250 may be used to transform the various image data, including reconstructions based thereon at each of the selected positions, to a selected reference frame to allow for generation of the stitched model 340 that does not include artifacts or errors due to the movement of the imaging system 31 which generates the projections at different positions of the imaging system 134 relative to the subject 28, as illustrated in FIG. 3.

Figure 6:
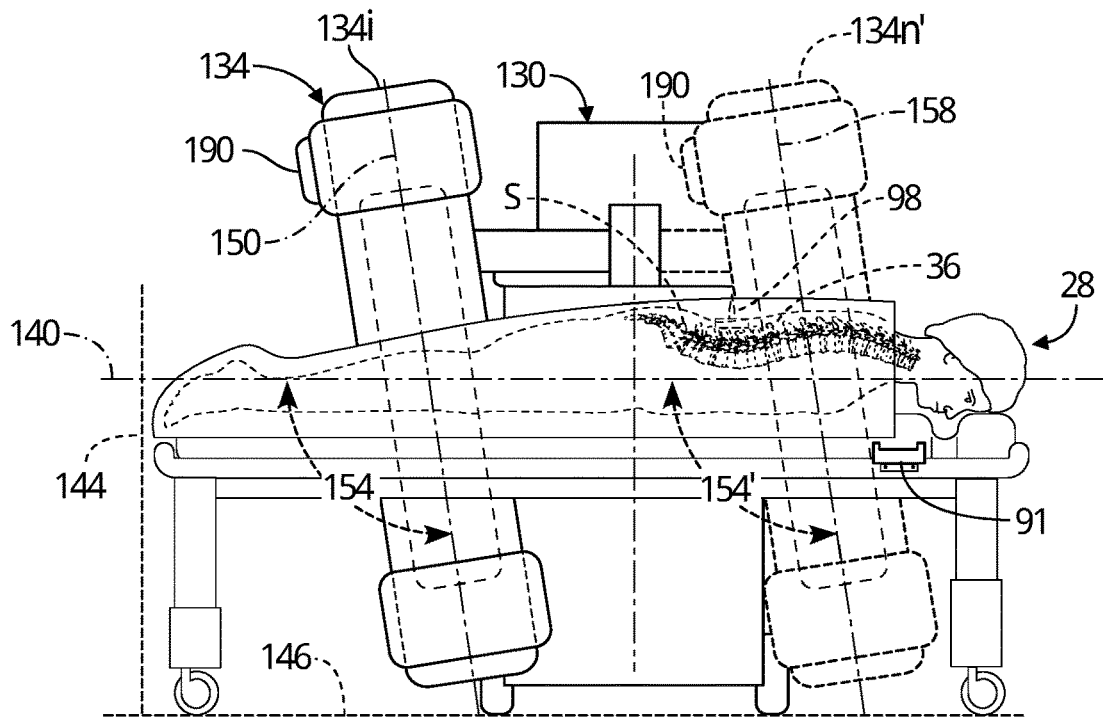
FIG. 6 is a schematic illustration of an aligned imaging system at two positions, according to various embodiments.

With continuing reference to FIG. 4, an alignment of the image data at position n to the image data at position i may be made based upon a transformation matrix as defined by Eq. 2 to determine an orientation or change of the gantry position during the acquisition between the initial position i and the second or subsequent position n in block 350.

$$T_{ISn' \to n} = T_{ISn' \to i} * T_{ISi \to n} \qquad \text{Eq. 2}$$

where $T_{ISn' \to n}$ is the transformation of the corrected position imaging system (IS) to the non-aligned IS position as a product of a transformation of the corrected IS position to the initial IS position and the initial IS position to the second IS position. The transformation allows for a determination of a transformation matrix that may be determined in block 354 as a correction matrix for the current or second image data at position n to the image data at the position i. The correction transformation is illustrated in Eq. 3 and accounts for a corrected position of the gantry n' that may also be referred as a virtual corrected position as illustrated in FIG. 6 that allows for a transformation of the image at position n. Eq. 3:

$$TISn'_{\to i} = \{RISn'_{\to i}, TrISn'_{\to i}\} \qquad \text{Eq. 3}$$

with $RISn'_{\to i}$ defining the rotation transform matching the initial and second image data coordinate systems orientation; and $TISn'_{\to i}$ defining the translation transform matching the initial and second image data coordinate systems origin. The transformation allows for an alignment of the two image data sets based upon a tracked position of the gantry 134 during the acquisition of the image data. With reference to FIG. 6, for example, the gantry at the position 134i includes the orientation or position relative to the axis 140, as discussed above. At the second position 134n, the gantry may have a different orientation relative to the axis 140. Although the gantry 134 may move generally along the axis in the direction that may also be referred to as the z-axis, the gantry may not maintain a substantially identical orientation relative to the axis 140 between the initial position 134i and the second position 134n. Nevertheless, the transformation, as discussed above in the process 250, may allow for a determination of a coordinate system that may be used to transform an orientation of the gantry 134 in the same orientation and only translated in the z-direction. The corrected or virtual position may be referred to as 134n' and have the angle 154', as illustrated in FIG. 6. Thus, the image data, such as the second projection 204, may be aligned to the image data acquired at the initial position 134i. Once the image data is corrected or a determination of a correction matrix is made in block 354 a combination of the image data may be made in block 360.

Figure 7:
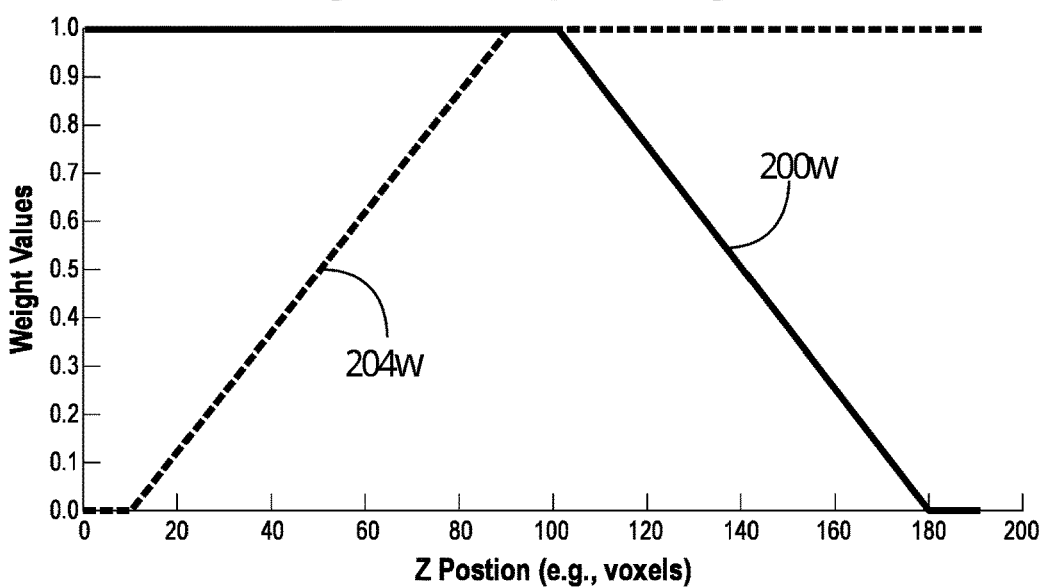
FIG. 7 is a graphical representation of a weighting function for generating a combined image data, according to various embodiments.

The combination of the image data at the initial position i and the image data at the second position n may be performed in appropriate manner. In various embodiments, for example, the image data may be stitched together by identifying appropriate or identical portions in stitching the related portions together. Such stitching techniques may include estimating the transformation by registering intrinsic features in both image data (which may include image data volumes) by a method such as, but not limited to, non-parametric, block matching image registration algorithms, fiducial- or image-based 3D image registration, as generally understood in the art. In various embodiments, for example, a weighted stitching process may occur and weights may be determined, optionally, in block 358. As discussed above, the various projections may be acquired with a selected amount of overlap. The amount of overlap may be known due to the known translation along the z-axis. Accordingly, the overlap amount 208' may be known for each of the projections. Along a distance of the overlap a selected weight may be provided or determined for each position along the image. For example, as illustrated in FIG. 7, based upon a position of the gantry 134 that moves along the axis 140, as discussed above which may refer to a z position or translation, a weight factor may be determined based upon the image data 200, 204. As illustrated in FIG. 7, for example, a weight factor 204w for voxels/pixels may increase as the z-position of the overlap and stitching moves closer to the second projection 204 and finally includes only voxels/pixels the second projection 204. Conversely a weight for the first projection 200 may decrease, as illustrated by wave line 200w, as the z-position moves away from the position of the initial projection 200. Accordingly a weight may be determined in block 358 to assist in the blending or stitching to perform or generate a combined image in block 360. It is understood, however, that weighting may not be required and that a selected position may be identified or determined to create a stitching between the two images.

The combined image may then be output in block 364. As discussed above a combined image may include the image 340, which may be displayed as the display image 120. The combined image 340 may registered to the subject 28 due to the tracking of the subject 28 with the subject tracker 98 and the tracking of the image system with the imaging system tracker 190 during image projection acquisition. Therefore, the image data 200, 204 may be individually registered to the subject 28 and the combination image or model 340 may also, therefore, be registered due to the inherent or included registration of the initial image data and the transformation in light of the navigation or tracked data as discussed above. This allows the combined image to include the dimension 344 that may include a selected dimension, such as by the user 24 and input to the imaging system 31, of the subject 28. The image 340 may be used for a selected procedure, such as a navigated procedure, that may allow for an illustration of the graphical representation 124 of the tracked instrument 20 relative to the subject 28 for the selected procedure. Therefore, an image that have a dimension, e.g., that is longer, than one that may be created with a single projection with the single projection with the imaging system 31 may be created and movement of the imaging system other than along a straight line, such as along the axis 140 that may also be referred to as the z-axis may be accounted for to create a selected or combined stitched image.

As discussed above, image data acquired of the subject may be corrected due to movement of the gantry 134 that is not only in a straight line and along an axis or plane, such as the axis 140. In various embodiments, movement of the gantry may be identified as movement along a z-axis which may be parallel and/or collinear to the axis 140.

In various embodiments, the movement of the gantry may not be only in the z-axis during the acquisition of a plurality of projections through the subject 28. In various embodiments, one or more portions may not be tracked. For example, tracking devices, including one or more of the imaging device tracking device 190 and/or the subject tracking device 98 may not be present. Further, the navigation systems 29 may not be present. It is understood that the image data may, however, be aligned according to various techniques, such as those discussed further herein. It is also understood that the various techniques may be combined, such as combining the navigation as discussed above to assist in aligning a plurality of projections to account for or correct for movement of the imaging device that is not only in a z-axis. Accordingly the navigation process, as discussed above, may or may not be used alone and may be used in combination with other processes, such as those discussed further herein.

Figure 8:
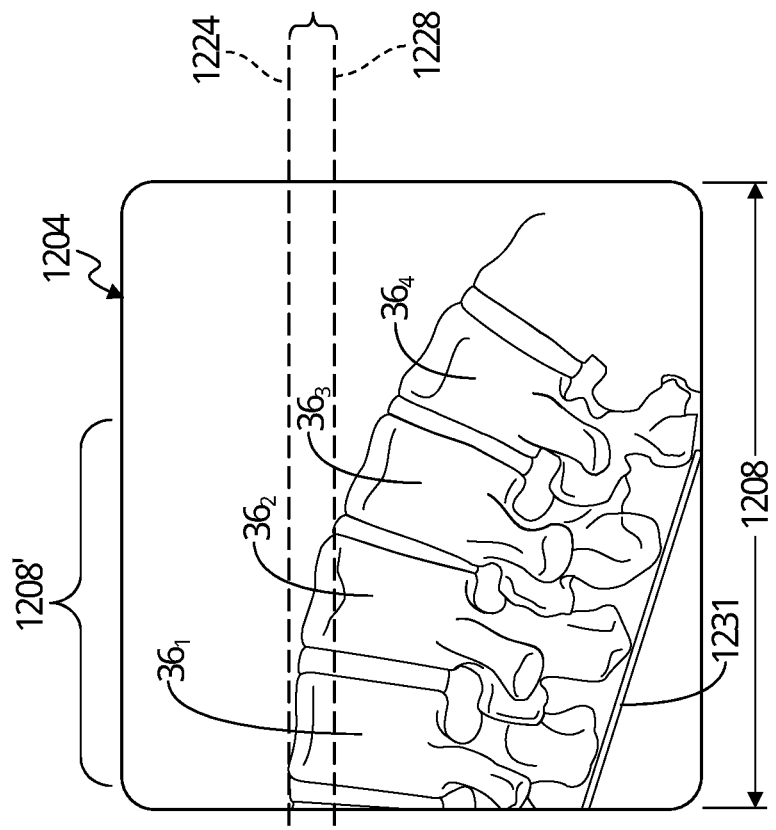
FIG. 8 is a schematic illustration of two projections, according to various embodiments.
Figure 8:
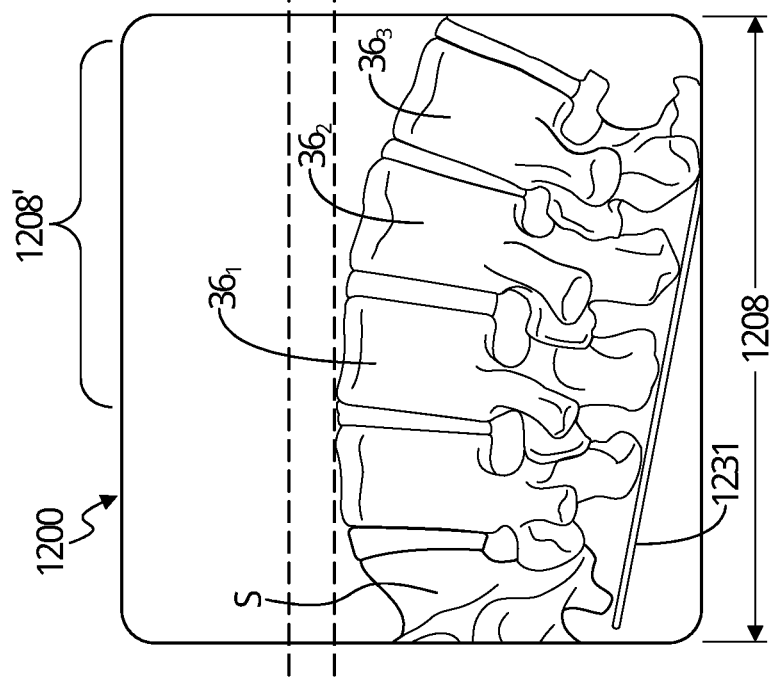

Turning reference to FIG. 8, two projections, such as a first projection 1200 and a second 1204 may be acquired with the imaging system 31. The projections 1200, 1204 may be similar or identical to the projections 200, 204, as discussed above. The projections 1200, 1204 may be acquired without the imaging system being tracked, the subject being tracked, or the use of the navigation system 29. The image projections 1200, 1204 may, therefore, include a misalignment distance 1200 between lines 1224 and 1228. In each of the projections 1200, 1204 selected vertebrae may be imaged which may be the same or different vertebrae, including the vertebrae $36_1$, $36_2$, $36_3$, $36_4$. In addition, each of the image projections may include selected features that may be selectively or optionally positioned relative to the subject 28, such as a fiducial member, such as a rod or member 1231.

Each of the projections 1200, 1204 may include a selected dimension, such as a length or dimension along the z-axis 1208. As discussed above, the dimension 1208 may be based on or limited on the dimensions of selected portions of the imaging system 31, such as a dimension of the detector, a dimension of the source, or other dimensions of the imaging device 31. Accordingly, the dimension 1208 may be a dimension that is a maximum dimension of any single projection based upon the imaging system 31. Further, as discussed above, when acquiring the projections a certain amount of overlap, such as an overlap distance 1208' may be included in each of the image projections 1200, 1204. The overlap 1280' may include portions that are imaged of the subject 28 that are identical or substantially identical between each of the projections. For example, the vertebrae $36_2$ and $36_3$ may be included entirely in both projections. In addition or alternatively a member, such as the rod 1231 may be included or imaged in both projections. The rod 1231 may include selected dimensions and geometry that may be predetermined and stored, such as in the memory 71. The imaging system or other selected processing systems, such as the processor 70, may recall the dimensions to assist in further procedures, such as in registration of the two projections 1200, 1204.

To assist in aligning the projections and to correct for the spatial difference 1220 that may be called due to movement of the imaging device, such as the gantry 134, various portions in the respective images 1200, 1204 may be identified and registered. For example the rod 1231 may be imaged and occur in both projections 1200, 1204, as illustrated in FIG. 8. Further, anatomical portions, such as the vertebrae $36_2$ may occur in both of the images 1200, 1204. These similar or identical portions may identified in both projections. Identification of the portions in both of the projections 1200, 1204 may be made manually, such as by identification by the user 24. In addition or alternatively, automatic identification may occur such as through selected automatic segmentation features or programs, such as model based anatomical segmentation algorithms such as, but not limited to, like deep learning image segmentation or supervised min-cut/max-flow image segmentation algorithms. Also, there may be combinations including the user identifying one or more voxels or pixels and a selected segmentation program identifying identical or similar (e.g., color, contrast gradient, etc.) voxels and/or edges relative to the voxels or selected portions.

In various embodiments, various high contrast features, such as an image of the rod 1231 and/or other selected features, such as the vertebrae $36_2$ may be identified and segmented in each of the projections 1200, 1204. Once the selected identical or common features are identified in each of the projections 1200, 1204, the projections may be registered to one another. The registration may include a transformation of pixels or voxels to align the respective projections 1200, 1204. The overlap region 1208' in each of the image projections 1200, 1204 may be used to perform the alignment. For example, if the rod 1231 is identified and segmented in both of the two projections 1200, 1204 these pixels or voxels may be aligned and the other pixels and voxels in the projection 1200, 1204 may be transformed or moved in a similar or identical manner to achieve alignment of the entire projection such that the first projection 1200 can be aligned with the second projection 1204. Selected transformations can include non-rigid, affine, and/or rigid transformations. In various embodiments, an entire object need not be imaged in both projections. For example, given a known geometry of the rod 1231, only a portion of the rod 1231 need be imaged in both projections to allow a registration. Further, as discussed above, registration between more than two projections, such as three, four, or more projections, may occur with the similar process.

It is further understood that the projections 1200, 1204 may include two-dimensional data, three-dimensional data, or any appropriate data type. For example, the projection 1200 may be a two-dimensional image data projection generated by the imaging system 31 at a first position, such as the position 134$i$ of the gantry and the second projection 1204 may also be a two-dimensional at the second position 134$n$ of the gantry. It is further understood, however, that each of the projections 1200, 1204 may be three-dimensional projections or models generated with image data at each of the respective positions 134$i$, 134$n$. In various embodiments, the imaging system 31 may generate three-dimensional image data by acquiring a plurality of projections relative to the subject 28. Therefore, the projections 1200, 1204 may be three-dimensional and the alignment may be a registration of three-dimensional image data or model between the projection 1200 and the second projection 1204.

Figure 9:
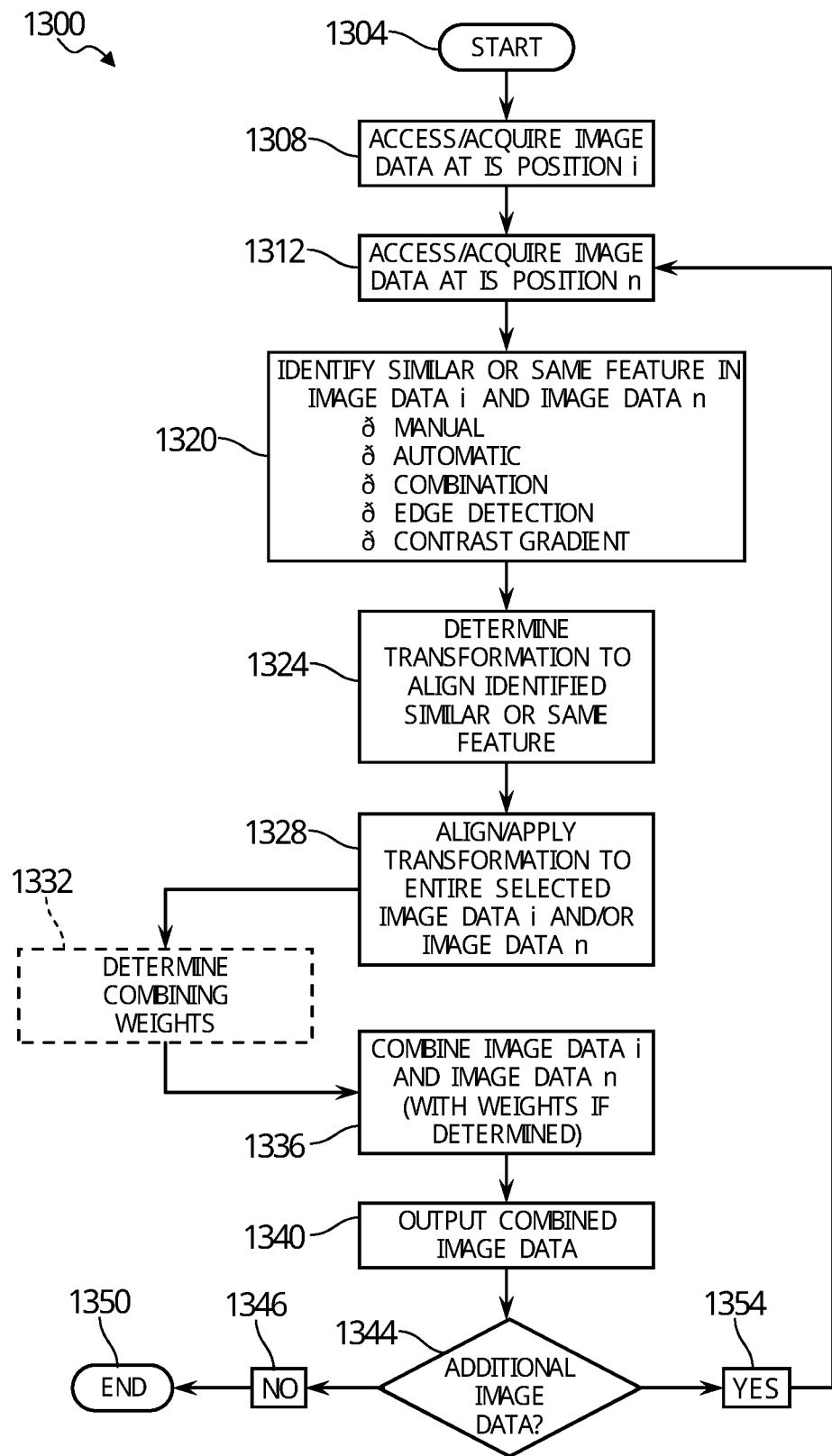
FIG. 9 is a flow chart of an alignment and combination process, according to various embodiments.

With continuing reference to FIG. 8 and additional reference to FIG. 9, a process 1300 may be used to access and align and combine the projections 1200, 1204. The process 1300 may begin in start block 1304 which may be similar to the start block 254, as discussed above. In various embodiments, the subject 28 may be positioned relative to the imaging system 31, such as in preparation for procedure, preparation to acquire image data for various purposes including planning a selected procedure, performing a selected procedure, or other appropriate processes. The start block 1304, therefore, may include various actions that may include preparing the imaging system 31, preparing the subject 28, or other appropriate steps to acquire or access image data.

After starting in block 1304, image data may be accessed or acquired at imaging system position i. As discussed above, the gantry 134 may be positioned at an initial or selected position 134$i$. The image data accessed or acquired in block 1308 may be image data that is acquired in real time of the subject 28, pre-acquired image data that is accessed, or any appropriate image data at a first or initial position. Image data may also be accessed or acquired at imaging system position n. As also discussed above, the imaging system 31 may be moved to a second or additional position including the gantry position 134$n$. Again the image data accessed or acquired in block 1312 may be image data that is acquired in real time, image data that is accessed that is pre-acquired, or any appropriate image data. In various embodiments, image data acquired at the initial position may include the projection 1200 and image data acquired or accessed at the second position 1312 may be the projection 1204.

In both of the image data, a similar or identical feature, such as the same rod 1231 and/or vertebrae $36_3$ may be identified in block 1320. As discussed above, for example, the rod 1231 and/or a portion of the rod 1231 may be identified in both of the projections 1200, 1204. The identification of the feature may be manual, automatic, or a combination of manual and automatic techniques. In various embodiments, the feature may be identified by use of edge detection or edge identification programs, such as segmentation, that are executed by a processor, such as the processor 70. Further, contrast gradients may be identified in the respective images that may be identified as the same or similar feature. Nevertheless the same or similar feature may be identified in both of the image data acquired or accessed in the respective blocks 1308, 1312. It is understood, therefore, that the identification may include various processes or steps that are carried out automatically, such by execution of program instructions with a processor, such as the processor 70

After identifying the same or similar feature in block 1320, a determination of a transformation to align the identified similar or same feature is made in block 1324. The determination of a transformation may include the required movement (e.g., translation) of image elements, such as pixels or voxels, to align the identified feature in one image projection to a second image projection. As discussed above, the rod 1231 may be identified in both image projections and a transformation may be determined to align the rod 1231 between both of the image projections 1200, 1204. Accordingly, a transformation may be determined in block 1324 to perform the alignment of the identified feature.

Once the transformation is determined in block 1324, the transformation may be applied or used to determine an image transformation that is applied to the entire image data i and/or the image data n in block 1328. As discussed above, the imaging system, including the gantry 134, may move between the acquisition of a first and second image data projection. The transformation may be applied to one or both of the image data to align both of image data 1200, 1204 to each other. In various embodiments, for example, the initial position may be determined to be the first position for the registration or alignment and the other image or images are aligned thereto. The transformation may be applied to the image data at position n to align the image data projection to the initial projection. Therefore, for example, the projection 1204 may have the transformation applied thereto to align the second projection 1204 to the first projection 1200.

Once the projections are aligned in block 1328, they may be combined or merged, as discussed above. In various embodiments, the combination may include determining one or more weights in block 1332. The determination of weights in block 1332 is optional and many include a weighting or gradient along a z-axis of one image data projection or the other during the combination, as discussed above and illustrated in FIG. 7.

The image data may be combined in block 1336 using the optional weights, if determined. The combination may include various combination procedures such as blending the image data acquired in block 1308 and the image data acquired in block 1312. Various combination techniques can include a blending such as those known as weighted averaging, gamma blending, and/or feathering.

After the image data is combined in block 1336, the combined image data may be output in block 1340. The output of the combined image data can include storing or saving the image data for later viewing, planning, or other appropriate actions. Outputting the combined image data may also or alternatively include displaying the image data for viewing by the user 24 or other appropriate techniques. In various embodiments, for example, the combined image data may be used to be viewed and/or for navigation of selected instruments. As discussed above, the image data may be registered to the subject 28 and, therefore, the navigation system 29 may use the combined image data output in block 1340 to assist in navigation, such as displaying a position graphical representation of the instrument 20.

After combining the image data in block 1340, a determination of whether additional image data is to be acquired in block 1344 may be made. If no additional image data is to be acquired a NO path 1346 may be followed to an end block 1350. Accordingly, the procedure 1300 may combine at least two image data projections, as discussed above, into a combined image data that may be output in block 1340.

If additional image data is determined to be acquired in block 1344, a YES path 1354 may be followed to access or acquire additional image data in block 1312. Accordingly, any additional image data may be accessed and/or acquired and registered or aligned to a selected reference, such as the initial or image data and IS position i in block 1308. The process 1300 may align a plurality or any appropriate number of projections that may be selected. As discussed above, for example, the single projection may include a dimension 1208. A combination of a selected number of image projections may be used to generate an image or image data having the dimension 344 as illustrated in FIG. 5. Therefore the process 1300 may also be used to generate the combined image data 340 that may be combined in block 1336 and output in block 1340.

As discussed above the process 250 may be used to generate the combined image 340. In addition and/or alternatively, the process 1300 may be used to generate the combined image 340. In addition, as discussed above, the procedures may be combined and/or augmented with each other. For example, the tracked location of the gantry 134 may be used to assist in determining a transformation of two image data projections. Also, identification of a similar feature in process 1300 may also be used to assist in the combining images, such as confirming the tracked position and/or augmenting the transformation between the first and second image projections. Therefore, the combination image data 340 may include or be generated with one or more selected procedures.

Regardless, the combination image data 340 may include the dimension 344 that is greater than the dimension 208, 1208 of any single projection, as discussed above. Therefore, the combined image 340 may include a larger dimension for various procedures, such as of the subject 28 including the vertebrae 36. The user 24 may view an image of a plurality of vertebrae in a single image greater than a single projection that may be generated with the imaging system 31. Further, as discussed above, as the image data is registered to the subject 28, the combination image 340 is also registered to the subject 28 and the navigation system 29 may, therefore, allow for navigation and tracking of tracked instruments, such as the instrument 20, relative to the combined projection 340. This allows the image 120 on the display 84 may be the combined image 340 with the icon or graphic representation 124 illustrated at the tracked or navigated position of the instrument 20 relative thereto. Also, the combined image 340 may be a two-dimensional and/or a three-dimensional image or reconstruction.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter, (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or čontroller˙ may be replaced with the term čircuit.˙ The term m̃odule˙ may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of generating a combined image from a plurality of image data, comprising:
   accessing a first image data acquired at a first imager position of an imager;
   accessing a second image data acquired at a second imager position of the imager;
   determining a feature having stored predetermined dimensions in the first image data;
   determining the feature in the second image data;
   determining an alignment transformation to align pixels or voxels of the feature between the first image data and the second image data without tracking a position of the imager;
   wherein the alignment transformation is operable to align the first image data and the second image data based on the determined alignment transformation without tracking a position of the imager; and
   outputting the alignment transformation operable to align the first image data and the second image data.

2. The method of claim 1, wherein determining the feature in the first image data and determining the feature in the second image data includes determining a high contrast gradient portion in the first image data and the second image data.

3. The method of claim 2, wherein the feature includes a member included in both the first image data and the second image data.

4. The method of claim 1, further comprising:
   transforming the second image data with the alignment transformation to generate an aligned second image data that is aligned to the first image data.

5. The method of claim 4, further comprising:
   combining the first image data and the aligned second image data to generate a combined image data.

6. The method of claim 5, further comprising:
   displaying the combined image based on the combined image data.

7. The method of claim 6, further comprising:
   registering the first image data to a subject;
   registering the second image data to the subject;
   wherein the combined image data and combined image are registered to the subject.

8. The method of claim 7, further comprising:
   navigating an instrument relative to the subject based on the combined image.

9. The method of claim 1, wherein the imager moves in at least two degrees of freedom between the first imager position and the second imager position;
   wherein the at least one of the degrees of freedom of movement is corrected to generate the aligned second image data based at least on the determined alignment transformation and the determined alignment transformation.

10. The method of claim 9, wherein the at least one of the degrees of freedom of movement includes movement of the imager outside of a Z-axis of movement of the imager.

11. The method of claim 1, further comprising:
acquiring the first image data with the imager; and
acquiring the second image data with the imager.

12. A method of generating a combined image from a plurality of image data, comprising:
accessing a first image data acquired at a first imager position of an imager;
accessing a final image data acquired at a final imager position of the imager;
determining at least a portion of a feature having stored predetermined dimensions included in both the first image data and the final image data;
determining an alignment transformation to align pixels or voxels of the feature between the first image data and the final image data without tracking a position of the imager;
determining an alignment transformation based on the alignment transformation to align the first image data and the final image data based on the determined alignment transformation, wherein the alignment transformation is operable to correct for misalignment of the first image data and the final image data in at least one degree of freedom of movement of the image between the first imager position and the final imager position that is outside a Z-axis movement of the imager without tracking a position of the imager; and
outputting the alignment transformation.

13. The method of claim 12, further comprising:
moving the imager to the first imager position;
moving the imager to the final imager position; and
moving the imager to the at least one intermediate imager position.

14. The method of claim 13, further comprising:
registering the first image data to a subject;
registering the intermediate image data to the subject;
registering the final image data to the subject; and
generating the combined image of all of the first image data, the intermediate image data, and the final image data based on the determined alignment transformation, wherein the determined alignment transformation is operable to align each of the first image data, the intermediate image data, and the final image data to at least a selected one of the first image data, the intermediate image data, or the final image data;
wherein the combined image includes the selected image dimension;
wherein the combined image is registered to the subject;
wherein the first image data and the second image data include an overlap portion.

15. The method of claim 12, wherein each of the first image data and the final image data include a dimension less than the selected image dimension.

16. The method of claim 12, further comprising:
tracking a position of an instrument relative to a subject;
displaying the combined image of the subject based on the first image data and the final image data that are combined based on the determined alignment transformation; and
displaying a graphical representation of the tracked instrument at the tracked position relative to the combined image.

17. A system to generate a combined image from a plurality of image data, comprising:
a processor system configured to execute instruction to:
access a first image data acquired at a first imager position of an imager;
access a final image data acquired at a final imager position of the imager;
determine at least a portion of a feature having stored predetermined dimensions included in both the first image data and the final image data;
determine an alignment transformation to align pixels or voxels of the feature between the first image data and the final image data without tracking a position of the imager;
determine an alignment transformation based on the alignment transformation to align the first image data and the final image data based on the determined alignment transformation, wherein the alignment transformation is operable to correct for misalignment of the first image data and the final image data in at least one degree of freedom of movement of the image between the first imager position and the final imager position that is outside a Z-axis movement of the imager without tracking a position of the imager; and
output the alignment transformation.

18. The system of claim 17, further comprising:
an imager configured to acquire the first image at the first imager position and the final image data at the final imager position.

19. The system of claim 17, further comprising:
a display to display the combined image based on the first image data and the final image data and a tracked position of an instrument relative to the combined image;
wherein the combined image is based on the first image data and the final image data combined based on the alignment transformation.

* * * * *

UNITED STATES PATENT AND TRADEMARK OFFICE
CERTIFICATE OF CORRECTION

PATENT NO. : 11,922,645 B2
APPLICATION NO. : 17/206032
DATED : March 5, 2024
INVENTOR(S) : Xavier Tomas Fernandez et al.

It is certified that error appears in the above-identified patent and that said Letters Patent is hereby corrected as shown below:

In the Specification

Column 3, Detailed Description, Line 25, Delete "O-armø" and insert --O-arm ø-- therefor Column 3, Detailed Description, Line 34, Delete "ZIEH M" and insert --ZIEHM-- therefor Column 3, Detailed Description, Line 49, Delete "Station" and insert --Stationø-- therefor Column 4, Detailed Description, Line 26, Delete "96" and insert --98-- therefor Column 7, Detailed Description, Line 42, Delete "24." and insert --29.-- therefor Column 7, Detailed Description, Line 44, Delete "24," and insert --29,-- therefor Column 9, Detailed Description, Line 64, Delete "24," and insert --29,-- therefor Column 11, Detailed Description, Line 20, Delete "TERI" and insert --$T_{ISRi}$-- therefor Column 13, Detailed Description, Line 51, Delete "positons" and insert --positions-- therefor Column 21, Detailed Description, Line 41, Delete "interpreter," and insert --interpreter;-- therefor Column 21, Detailed Description, Line 46, Delete "SQL" and insert --SQL,-- therefor Signed and Sealed this
Tenth Day of December, 2024

Katherine Kelly Vidal
*Director of the United States Patent and Trademark Office*